United States Patent
Nascetti et al.

(10) Patent No.: US 7,233,004 B2
(45) Date of Patent: Jun. 19, 2007

(54) X-RAY EXAMINATION APPARATUS INCLUDING A DOSIMETER

(75) Inventors: Augusto Nascetti, Aachen (DE); Michael Overdick, Langerwehe (DE)

(73) Assignee: Koninklijke Philips Electronics, N.V., Eindhoven (NL)

( * ) Notice: Subject to any disclaimer, the term of this patent is extended or adjusted under 35 U.S.C. 154(b) by 260 days.

(21) Appl. No.: 10/513,208

(22) PCT Filed: Apr. 29, 2003

(86) PCT No.: PCT/IB03/01642

§ 371 (c)(1),
(2), (4) Date: Nov. 2, 2004

(87) PCT Pub. No.: WO03/093869

PCT Pub. Date: Nov. 13, 2003

(65) Prior Publication Data

US 2005/0173640 A1    Aug. 11, 2005

(30) Foreign Application Priority Data

May 3, 2002    (DE) .............................. 102 19 927

(51) Int. Cl.
*G01J 1/00* (2006.01)
*H05G 1/64* (2006.01)

(52) U.S. Cl. ............................ 250/370.09; 250/370.08; 378/98.8; 378/87; 378/97; 378/65

(58) Field of Classification Search ........... 250/370.09, 250/370.08, 370.078; 378/98.8, 87, 97, 207, 378/65

See application file for complete search history.

(56) References Cited

U.S. PATENT DOCUMENTS

| | | | | |
|---|---|---|---|---|
| 4,053,774 A | * | 10/1977 | Berdahl | 378/97 |
| 4,286,157 A | * | 8/1981 | Eickel et al. | 250/370.07 |
| 5,181,234 A | * | 1/1993 | Smith | 378/87 |
| 5,184,018 A | | 2/1993 | Conrads et al. | |
| 5,262,649 A | * | 11/1993 | Antonuk et al. | 250/370.09 |
| 5,444,756 A | * | 8/1995 | Pai et al. | 378/98.8 |
| 5,844,965 A | * | 12/1998 | Galkin | 378/207 |
| 5,962,856 A | | 10/1999 | Zhao et al. | |
| 6,842,502 B2 | * | 1/2005 | Jaffray et al. | 378/65 |
| 2004/0251420 A1 | * | 12/2004 | Sun | 250/370.09 |
| 2006/0153330 A1 | * | 7/2006 | Wong et al. | 378/65 |

FOREIGN PATENT DOCUMENTS

| EP | 0 308 217 | 3/1989 |
|---|---|---|
| EP | 1 179 741 A2 | 2/2002 |
| JP | 09 010191 | 1/1997 |

* cited by examiner

*Primary Examiner*—David Porta
*Assistant Examiner*—Faye Boosalis

(57) ABSTRACT

The invention relates to an arrangement which includes a radiation source (1) and a radiation sensor device (3) for forming image signals (Bn), the radiation sensor device (3) being associated with a read-out circuit arrangement (4) for the amplification/processing of image signals (Bn) read out, there also being provided at least one dosimeter (42) which is arranged to measure a radiation dose. The invention also relates to an X-ray examination apparatus and to a method for the processing of X-ray images. In order to realize an arrangement and a method whereby a high image quality can be achieved for the acquired images, it is proposed to apply a dose signal (Dn), produced by at least one dosimeter (42), to at least the read-out circuit arrangement (4).

20 Claims, 3 Drawing Sheets

X-RAY EXAMINATION APPARATUS INCLUDING A DOSIMETER

The invention relates to an arrangement which includes a radiation source and a radiation sensor device for forming image signals, the radiation sensor device being associated with a read-out circuit arrangement for the amplification/processing of image signals read out, there also being provided at least one dosimeter which is arranged to measure a radiation dose. The invention also relates to an X-ray examination apparatus which includes an X-ray tube, an X-ray detector, a read-out circuit arrangement and an image processing device. The invention also relates to a method of processing X-ray images, in which method X-rays emitted by an X-ray tube are conducted to an X-ray detector which is arranged to generate image signals, comprises sensors and is associated with at least one dosimeter, said dosimeter generating at least one dose signal which is indicative of the intensity of X-rays.

The invention can be used in the field of image pick-up devices. The radiation sensor device may then be a light-sensitive sensor device as well as a sensor device which is sensitive to X-rays. Light-sensitive sensor devices are used, for example, in the photographic technique. Sensor devices which are sensitive to X-rays are used in particular in the medical field but also in the field of materials analysis or in the field of security. The sensor devices may also be sensitive to a plurality of types of radiation of different wavelength.

Because only comparatively small radiation doses are used for medical examinations in order to ninimize the radiation dose whereto the patient to be examined is exposed, the image signals formed from the X-rays are very susceptible to interference and generally have only a very low level, thus giving rise to sensitivity problems in the sensor devices. The foregoing necessitates complex post-processing of the image signals, so that they can also be further processed when they have a very low level. An increase of the radiation dose so as to generate a stronger image signal is thus avoided.

Generally speaking, radiation is emitted by a radiation source in such arrangements. The radiation source may then be constructed as a light radiation source or as an X-ray tube. The radiation sensor device converts the incident radiation, for example, into charge carriers, or into radiation of a different wavelength, which is detected by sensors and wherefrom, for example, electrical image signals are formed. A different radiation dose is then incident on the individual areas or points of the sensor surface. In the medical field X-rays are attenuated to a varying extent due to the varying absorption properties of the bones and the tissue of the patient to be examined, thus giving rise to differences between the image signals which ultimately result in the commonly known X-ray images. The radiation sensor device is succeeded by a read-out circuit arrangement which performs, for example, amplification and conversion of the analog image signals into digital image signals. The image signals are individually applied to the read-out circuit arrangement, the amplification and conversion yielding an overall image signal which is displayed/output on, for example, a monitor or another output medium via an image processing device.

EP 0440282 discloses an embodiment of an arrangement with a read-out circuit which is conceived in particular for X-rays. A further arrangement with a dosimeter is disclosed in EP 00308217.9.

The number of image signals to be transferred from the radiation sensor device to the read-out circuit arrangement is usually very large, so that a large amount of time is required for this purpose. Such radiation sensor devices are also used inter alia to form moving images, the image repetition frequency required for high quality imaging then necessitating a very high data throughput within a very short period of time. Limiting the data throughput leads to a limitation of the display quality.

Therefore, it is an object of the invention to provide an arrangement and a method whereby a high display quality can be achieved for images to be acquired.

This object is achieved by means of an arrangement which includes a radiation source and a radiation sensor device for generating image signals, the radiation sensor device being associated with a read-out circuit arrangement for the amplification/processing of image signals read out, there also being provided at least one dosimeter which is arranged to measure a radiation dose, and in which at least one dose signal generated by the dosimeter can be applied at least to the read-out circuit arrangement.

The invention is based on the idea that a radiation dose signal intended to control the radiation capacity of the radiation source can be advantageously used in accordance with the invention for influencing the processing stages of a radiation device.

Depending on the relevant type, dosimeters are integrated in the sensor device or are arranged, for example, in the form of an ionization chamber, in front of the sensor device. They generate a dose signal which is proportional to the amount of radiation occurring.

Until now this dose signal was used exclusively for the control of the radiation source. In accordance with the invention the information contained in the dose signal is also used to influence the downstream components in that at least one dose signal is applied to the read-out circuit arrangement.

To this end, in an advantageous embodiment of the invention the sensor device consists of a plurality of single sensors. The larger the number of sensors in relation to the surface area of the sensor device, the higher the resolution of the image formed will be. For simple applications it already suffices to generate only one dose signal for the entire sensor device. In that case only a single dosimeter is provided. In the case of high resolution sensor devices, a dosimeter may be associated with each individual sensor in an extreme case. Depending on the relevant application, it is advisable to form a mean dose signal for a group of sensors. The formation of one or more mean dose signals can take place either already in the sensor device or in a unit succeeding the sensor device.

Parameters of the read-out circuit arrangement can be changed in an advantageous embodiment of the invention. The dose signal is generated simultaneously with the image signals upon exposure of the sensor device to be incident rays. The dose signal is then applied to the read-out circuit arrangement earlier or at least no later than the image signals. The read-out circuit arrangement comprises, for example, amplifiers for amplifying the image signals which are usually very weak and possibly also noisy. Furthermore, in order to convert the analog image signals into digital image signals there are also provided A/D converters which combine the individual image signals so as to form an overall image signal which is then suitable for further processing. Depending on the dose signal or the plurality of dose signals, parameters of the image signals, for example, the necessary amplification of the image signals, can be changed. To this end, for example, a gain factor for the image signals is associated with the individually measured dose signals in a look-up table which is stored in a memory. From the amount of radiation incident on the corresponding sensor, and the dose signal generated therefrom, there is thus determined an individual gain factor whereby the image signal read from this sensor is amplified.

In an advantageous embodiment of the invention a parameter, for example, an offset or gain factor, of the image signals is changed to the same extent for all image signals of the sensor device, that is, in dependence on the dose signal. The influencing of other parameters, for example, the current/voltage supply for the read-out circuit arrangement, is also possible. The type of filtering of all or only individual image signals can also be influenced.

The changing of the parameters in dependence on the dose signal or the dose signals yields an enhanced overall image quality and the arrangement can then also be used for a larger dynamic range.

In an advantageous embodiment of the invention the image signals are applied to the read-out circuit arrangement in dependence on whether the dose signal exceeds or does not reach a threshold value, for example, in order to prevent amplification of image signals from overexposed sensor areas. Because an exposed or irradiated object usually does not cover the entire surface area of the sensor device, individual areas will be struck by direct radiation Such direct radiation image signals, however, usually are not of interest. Moreover, the usually strong radiation in such direct radiation areas produces an image signal which is very strong in comparison with the other image signals of the irradiated object and is applied to the read-out circuit arrangement. This high-level image signal usually leads to saturation in the correspondingly associated amplifiers. On the basis of the likewise high dose signal from such directly irradiated areas the image signals from these areas can be switched off, or excluded from amplification, by comparison with a threshold value so that on the one hand the image signals of the overexposed areas are not applied to the read-out circuit arrangement and on the other hand the amplifiers are not driven into the saturation range either. Furthermore, an examination zone can be defined on the basis of selectable threshold values.

The radiation source in a preferred embodiment of the invention is formed by an X-ray tube while the radiation sensor device is formed by an X-ray detector.

The invention can be carried out particularly advantageously in X-ray detectors which consist of a plurality of sensors which are sensitive to X-rays. The sensors are then arranged, for example, in rows and columns in the form of a matrix. The dosimeter measures the radiation dose occurring during the irradiation. The dose signal is applied to the read-out circuit arrangement before the image signals. It is then advantageous to perform the dose measurement for groups of sensors in the X-ray detector, because the differences in radiation dose between neighboring sensors are negligibly small. Preferably there are formed so-called superpixels which consist of a group of individual sensors. In this manner the X-ray detector supplies two signals per unit of time for each individual sensor. A first signal is a mean dose signal which may be the same for a plurality of sensors. The further signal is an image signal which is read out from each individual sensor and has been formed from the incident amount to radiation. These two signals are applied to the read-out circuit arrangement in accordance with the invention.

In a further embodiment of the invention the mean dose signal of a superpixel is subtracted from the image signals associated with this superpixel in the read-out circuit arrangement, so that smaller difference signals are formed from the image signals. Because the mean dose signal offers an indication as regards the value range in which the incident radiation is situated, the formation of the difference signal ensures that only the deviation relative to said mean signal is further processed. A calculation unit may be provided for this purpose. Subsequently, the mean dose signal and the relevant image signals are converted into digital signals by A/D converters included in the read-out circuit arrangement The amount of image signals to be processed is thus reduced.

In an X-ray sensor device consisting of 1024×1024 individual sensors or pixels with a superpixel for radiation dose measurement which consists of each time 64×64 sensors, for example, 8 bits can be used for converting the mean dose signal and 8 bits for converting the difference signal. Thus, for each image or frame 1024×1024×8 bits and additionally 16××8 bits for the mean dose signals would have to be transferred, so overall only approximately 8 Mbit/frame in the case of a resolution of 16 bits. Without the arrangement in accordance with the invention, however, 16 Mbit/frame would have to be transferred for a resolution of 16 bits. The range of values of the digitization for the mean dose signal and that for the difference signals preferably overlap a few bits so as to cover a larger dynamic range, said overlap not being taken into account in the above numerical example.

In a further embodiment of the invention the mean dose signal of the X-ray detector is used to adapt the conversion range of the A/D converters. This enables the same signal resolution for the same signal ranges and increases the dynamic range of the X-ray detector. In methods which are known from the state of the art the dynamic range of the X-ray detector is usually increased only while accepting non-linear disturbances in the image signals, for example, by utilizing logarithmic amplifiers.

In a further embodiment of the invention the dose signal is used to adjust the gain factor of the amplifiers for amplifying the image signals read out from the X-ray sensor device in the read-out circuit arrangement. The dynamic range of the X-ray sensor device is thus increased, without it being necessary to form a difference signal from the mean dose signal and the relevant image signals. Moreover, using the dose signal from a group of sensors, for example, a column of sensors, it is advantageously possible to adjust only the gain factor of the relevant column to be read out in the X-ray detector.

The sensor arrangement includes large-area electronic circuitry which is advantageously realized by means of a thin-film technique. The invention can also be used in sensor devices utilizing electronic circuitry from crystalline silicon, for example, realized in CMOS technology. In the case of X-ray detectors the conversion of X-ray quanta can be performed by means of scintillators or directly converting materials.

The object is also achieved by means of an X-ray examination apparatus which includes an X-ray tube, an X-ray detector for generating image signals, a read-out circuit arrangement which is associated with the X-ray detector in order to amplify/process image signals read out, at least one dosimeter which is arranged to measure a radiation dose, and an image processing device, in which apparatus a dose signal generated by the dosimeter can be applied to the read-out circuit arrangement and/or the image processing device. The additional information of the dose signal is then also applied to the image processing unit in order to influence the overall image signal during the further processing. For example, the dose signals may already produce a coarsely rastered representation of the overall image. This represents low-pass filtered image information which can be advantageously used directly in the image processing, for example, for the formation of a "multi-resolution" decomposition of the image information.

Time can be saved by applying the dose signal to the read-out circuit arrangement in accordance with the invention, that is, notably by reducing the redundancy in the image signals to be transferred Furthermore, the A/D converters may be proportioned so as to be smaller, thus enabling faster conversion.

The object is also achieved by means of a method for X-ray image processing in which X-rays emitted by an X-ray tube are conducted to an X-ray detector which is arranged to generate image signals, comprises sensors and is associated with at least one dosimeter, the dosimeter generating at least one dose signal which is indicative of the intensity of X-rays, said dose signal being applied to a read-out circuit arrangement no later than simultaneously with the image signals in order to influence individual parameters of the image signals of the individual sensors and/or to influence the totality of image signals.

The invention will be described in detail hereinafter with reference to the drawings. Therein:

Figure 1:
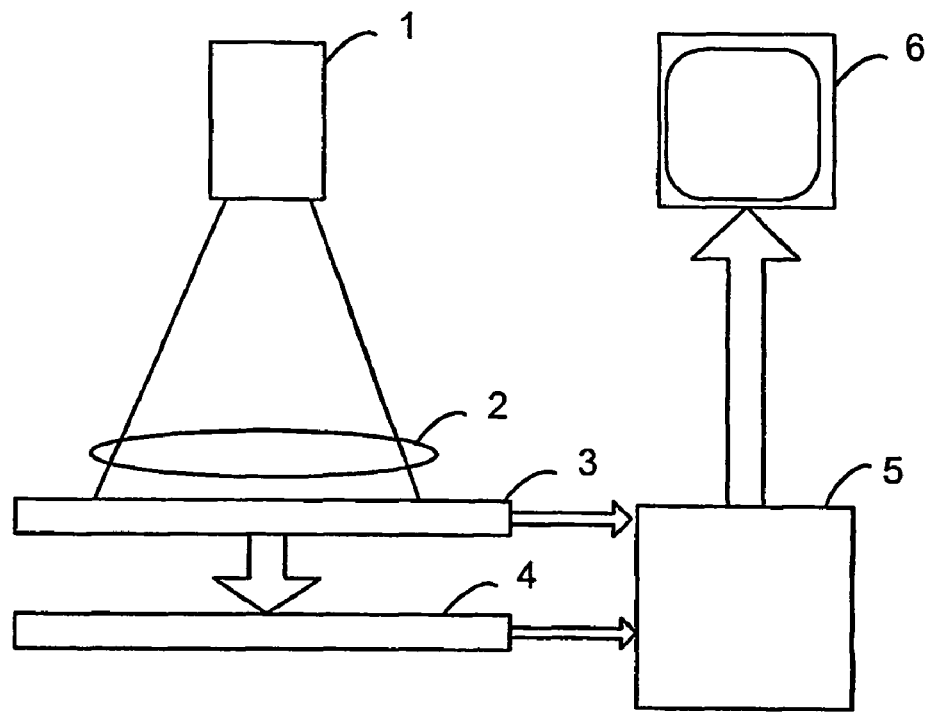
FIG. 1 shows an X-ray examination apparatus.

FIG. 1 shows an X-ray examination apparatus in which an X-ray tube 1 emits X-rays which are first incident on a patient 2 or an object to be examined and subsequently on an X-ray detector 3. The X-ray detector 3 comprises a layer (not shown) in which the X-rays are converted into visible light radiation. The light radiation is detected by light-sensitive sensors in which it is converted into electric charge carriers. According to another possibility the incident X-rays are converted directly into electric charge carriers. The electric charge carriers are applied as image signals to a read-out circuit arrangement 4 in which they are amplified and converted into digital signals. From the numerous individual image signals from the numerous individual sensors of the X-ray detector the read-out circuit arrangement 4 generates a common image signal which is applied to an image processing unit 5 in which the image is further processed. The image produced by the image processing unit can be output by an output unit, for example, a monitor 6.

Figure 2:
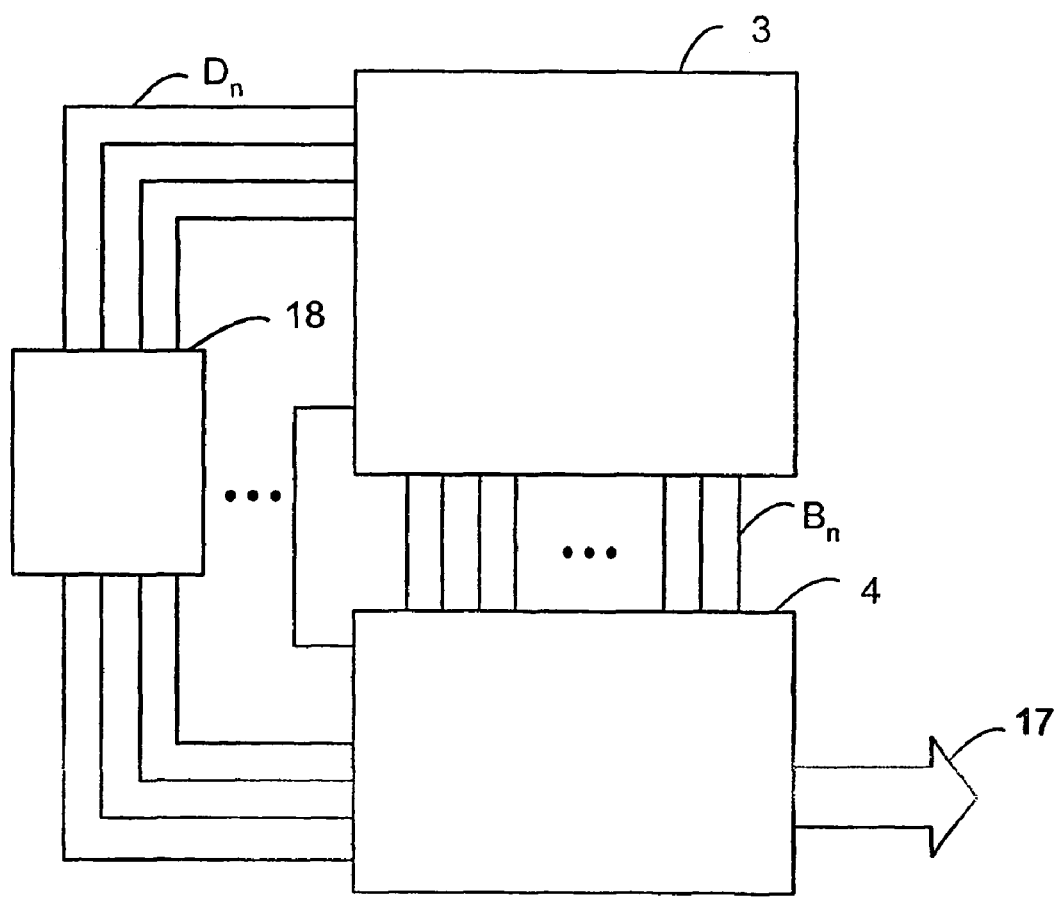
FIG. 2 is a diagrammatic representation of an arrangement in accordance with the invention.

FIG. 2 shows an arrangement in accordance with the invention. The X-ray detector 3 comprises a plurality of single sensors (not shown), the X-ray detector 3 also being associated with a dosimeter (not shown either). The single sensors convert the X-rays into electric charge carriers which are applied to the read-out circuit arrangement 4 as image signals $B_n$. The dosimeter generates a dose signal $D_n$ which is proportional to the incident X-ray dose and, in accordance with the invention, is also applied to the readout circuit arrangement 4. In FIG. 2 a plurality of dose signals $D_n$ is generated, because a plurality of dosimeters is arranged in the X-ray detector 3 in the present embodiment. The detected dose signals $D_n$ are applied to a look-up table 18 in which a gain factor is associated with each dose value of a dose signal $D_n$. This gain factor is applied to the corresponding amplifier in the read-out circuit arrangement 4 which amplifies the image signal $B_n$ which originates from the region or the pixel on which the corresponding dose $D_n$ was measured.

Figure 3:
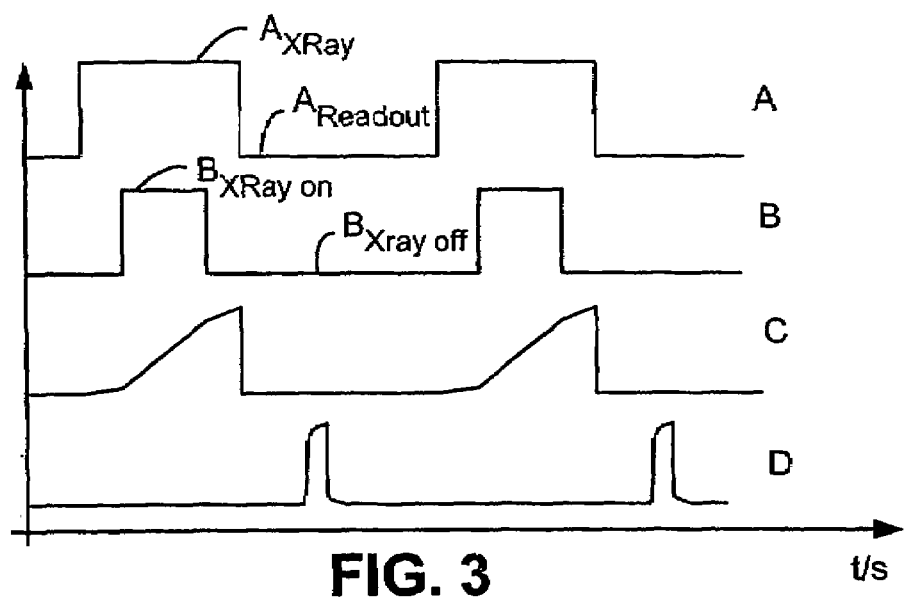
FIG. 3 is a time diagram of the X-ray exposure, the dose signal, and the image signal.

FIG. 3 shows a time diagram The signal waveform A shows the time window $A_{XRay}$ in which reading does not take place. $A_{Readout}$ denotes the time window in which the image signals $B_n$ are read out. The signal waveform B shows the time window $B_{XRay\ on}$ in which exposure by means of X-rays takes place. In the remaining time $B_{XRay\ off}$ the X-ray tube does not emit X-rays. The signal waveform C shows the rise of a dose signal $D_n$ as a function of the time of the X-ray exposure within the time window $A_{XRay}$. The dose signal is then available already during the exposure and prior to the reading out. The signal waveform D shows the instant at which the image signal $B_n$ of a pixel is read out within the time window $A_{Readout}$.

Figure 4:
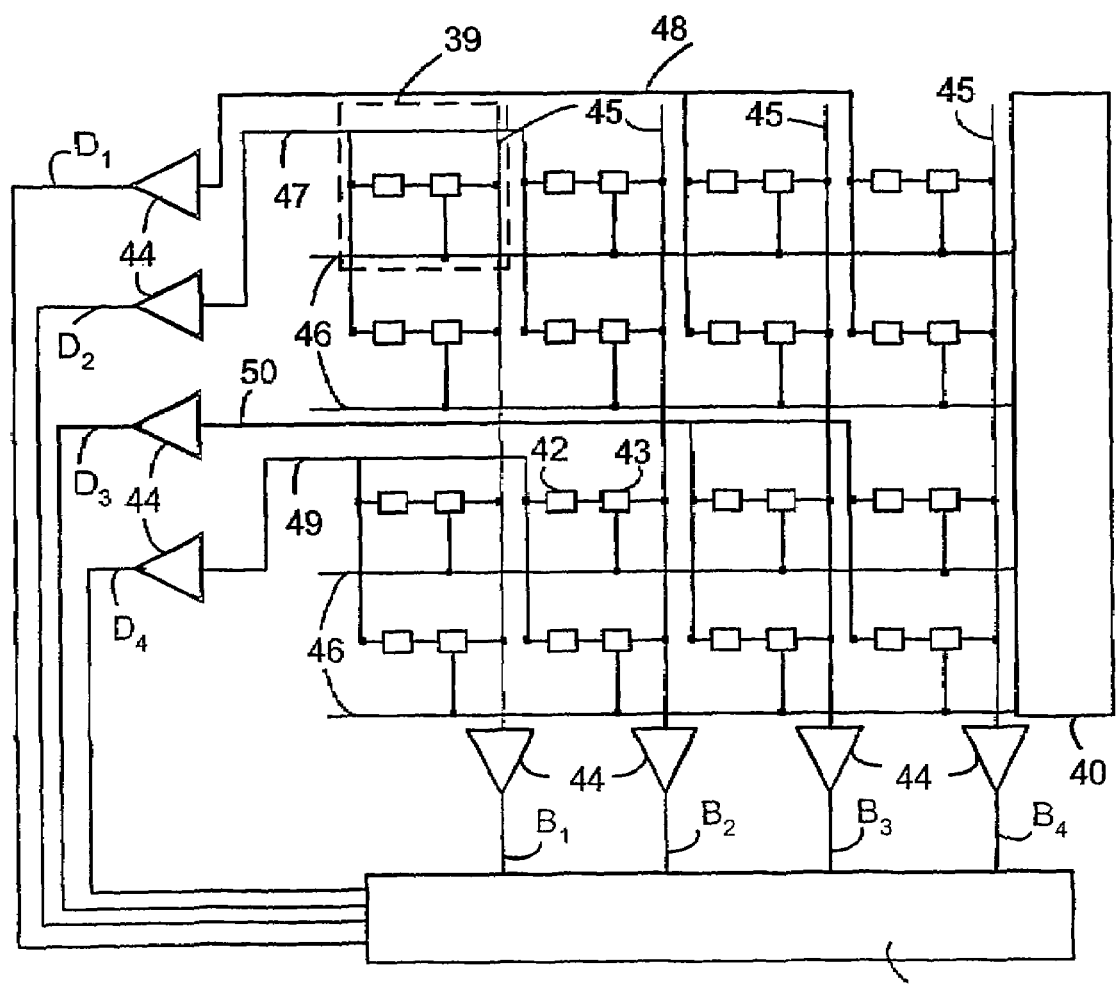
FIG. 4 shows a detail of a sensor with a dosimeter.
Figure 5:
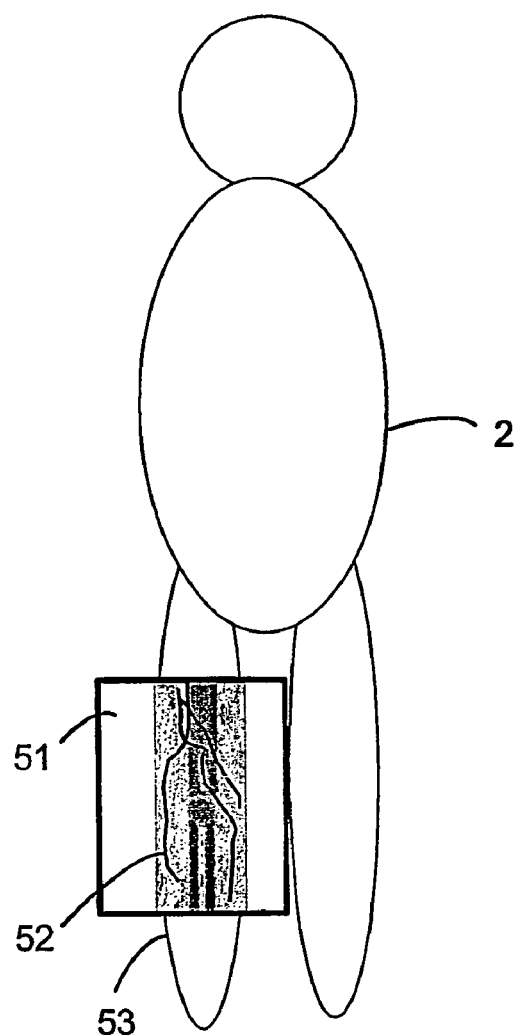
FIG. 5 is a representation of an overexposed area and the region of interest (ROI)

FIG. 4 shows a detail of an X-ray detector 3. The X-ray detector comprises a plurality of single sensors or pixels. For the sake of clarity, only one sensor 39 is explicitly indicated. The detail shown comprises 16 sensors in total. Each sensor includes a dosimeter 42 and a switching unit 43; a sensor also includes a light-sensitive or X-ray sensitive element 67 and a charge carrier collector element 65 (not shown). Via control leads 46, the row control unit 40 controls the sensors of each time one row, so that the charge carriers generated can be applied as image signals $B_1$ to $B_4$, via the read-out leads 45, to the amplifiers 44 and subsequently to the read-out circuit arrangement 4. The X-ray dose in each sensor is measured over the exposure time by means of the dosimeters 42. In the present embodiment the dose signals from each time four neighboring sensors are combined and averaged. The mean dose signals $D_n$ of the each time four sensors are applied, via the read-out leads 47 to 50, to the amplifiers 44. The dose signals $D_1$ to $D_4$ thus generated are applied to the read-out circuit arrangement 4, said amplifiers 44 forming part of the read-out circuit arrangement FIG. 5 shows a patient 2 whose leg has been X-rayed. The X-ray image 53 formed contains directly irradiated regions 51 and a region 52 in which the X-rays have been attenuated by the patient. This region 52 is also referred to as the Region Of Interest (ROI). Sensors which are situated in the region 51 have a very high dose signal as opposed to those which are situated in the region 52. Using a threshold value, the amplifiers in the read-out circuit arrangement can be switched off for all image signals for which the dose signal exceeds the threshold value, or amplification of the corresponding image signals can be inhibited. As a result, only the image regions which are actually of interest are further amplified and displayed, without falsifying overexposed regions being displayed.

Figure 6:
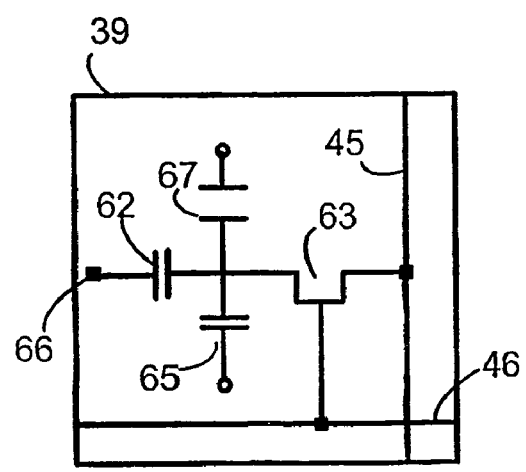
FIG. 6 shows an embodiment of a sensor element.

FIG. 6 shows a single sensor 39. This sensor includes a light-sensitive or X-ray sensitive element 67, a capacitor 65 which serves as a charge carrier collecting element, and a switching transistor 63. A capacitor 62 is provided as a dosimeter. The control lead controls the switching transistor 63 in such a manner that the charge carriers collected in the capacitor 65 can be read out via the read-out lead 45. The dose signal is present on the junction 66 wherefrom it can be read out directly via read-out leads (not shown). However, as is shown in FIG. 4, it can also be combined with the dose signals from other sensors so as to be averaged.

The invention claimed is:

1. An apparatus including: a radiation source and a radiation sensor device for forming image signals, the radiation sensor device being associated with a read-out circuit arrangement for the amplification/processing of image signals read out, there also being provided at least one dosimeter which is arranged to measure a radiation dose, and in which at least one dose signal generated by the dosimeter is applied at least to the read-out circuit arrangement, wherein each dose signal corresponds to at least one of the image signals, wherein the image signals are applied to the read-out circuit arrangement in dependence on whether a threshold value of the dose signal is exceeded or not reached, wherein only the image signals having a corresponding dose signal below the threshold value are amplified.

2. The apparatus of claim 1, wherein the dosimeter is integrated in the radiation sensor device.

3. The apparatus of claim 2, wherein the radiation sensor device consists of a plurality of single sensors.

4. The apparatus of claim 3, wherein at least one dosimeter is associated with at least one sensor of the radiation sensor device.

5. The apparatus of claim 4, wherein at least one dosimeter generates each time a dose signal from groups of sensors and that group-wise influencing of the image signals formed by the group of sensors takes place in the read-out circuit arrangement.

6. The apparatus of claim 1, wherein the dose signal is applied to the read-out circuit arrangement no later than simultaneously with the image signals of the radiation sensor device.

7. The apparatus of claim 1, wherein parameters of the read-out circuit arrangement are influenced by means of the dose signal.

8. The apparatus of claim 7, wherein parameters of the image signals are changed in dependence on the dose signal.

9. The apparatus of claim 1, wherein the totality of image signals of the radiation sensor device are changed in dependence on the dose signal.

10. The apparatus of claim 1, further comprising one or more amplifiers each having a gain factor, wherein the gain factor is adjusted based on the dose signal and wherein at least one of the image signals is amplified by the amplifier based on the gain factor.

11. The apparatus of claim 1, wherein in the radiation sensor device at least one mean dose signal is formed for at least two single sensors from the dose signals generated by the dosimeters.

12. The apparatus of claim 1, wherein in the read-out circuit arrangement the dose signal of a sensor is subtracted from the image signal associated with this sensor, the resultant difference signal being intended for further processing.

13. The apparatus of claim 1, wherein the radiation source is constructed as an X-ray tube and the radiation sensor device is constructed as an X-ray detector.

14. An X-ray examination apparatus which includes an X-ray tube, an X-ray detector for generating image signals, a read-out circuit arrangement which is associated with the X-ray detector in order to amplify/process image signals read out, at least one dosimeter which is arranged to measure a radiation dose and generate dose signals, and an image processing device, wherein each of the dose signals corresnonds to at least one of the image signals, wherein the image signal is applied to the read-out circuit arrangement in dependence on whether a threshold value of the dose signal is exceeded or not reached, wherein only the image signals having a corresponding dose signal below the threshold value are amplified.

15. A method for processing X-ray images, in which method X-rays emitted by an X-ray tube are conducted to an X-ray detector which is arranged to generate image signals, comprises sensors and is associated with at least one dosimeter, the dosimeter generating at least one dose signal which is indicative of the intensity of X-rays, said dose signal being applied to a read-out circuit arrangement no later than simultaneously with the image signals in order to influence at least one of individual parameters of the image signals of the individual sensors and the totality of image signals, wherein each dose signal corresponds to at least one of the image signals, wherein the image signals are applied to the read-out circuit arrangement in dependence on whether a threshold value of the dose signal is exceeded or not reached, wherein only the image signals having a corresponding dose signal below the threshold value are amplified.

16. A method of forming X-ray images comprising the steps of:
   emitting X-rays from a source;
   detecting the emitted X-rays;
   using at least a portion of the detected X-rays to form image information;
   gathering X-ray dose signals representative of dosage information; and
   using the gathered dosage information with the image information to influence individual parameters of the image information prior to forming an image, wherein each of the dose signals corresponds to a portion of the image information, wherein image signals are applied to a read-out circuit in dependence on whether a threshold value of the dose signals is exceeded or not reached, wherein only the image signals having a corresponding dose signal below the threshold value are amplified.

17. The method of claim 16, wherein the step of using the gathered dosage information occurs substantially simultaneously with the step of using the detected X-rays to form image information.

18. The method of claim 16, further comprising determining a mean dose signal from a plurality of dose signals; and determining a difference signal from the image signals and the mean dose signal.

19. The method of claim 16, further comprising adjusting a gain factor of at least one amplifier of the read-out circuit based at least in part on the dose signals.

20. The method of claim 16, further comprising determining a type of filtering for at least one of the image signals based at least in part on the dose signals.

* * * * *